United States Patent [19]
Reimels et al.

[11] Patent Number: 5,505,736
[45] Date of Patent: Apr. 9, 1996

[54] SURGICAL FASTENER WITH SELECTIVELY COATED RIDGES

[75] Inventors: William J. Reimels, Brockton; John Prudden, Jr., Newtonville, both of Mass.

[73] Assignee: American Cyanamid Company, Wayne, N.J.

[21] Appl. No.: 525,496

[22] Filed: Sep. 8, 1995

Related U.S. Application Data

[63] Continuation of Ser. No. 837,458, Feb. 14, 1992, abandoned.

[51] Int. Cl.$^6$ .................................................. A61B 17/56
[52] U.S. Cl. ............................... 606/72; 606/73; 606/76
[58] Field of Search ...................... 606/62, 65, 72, 606/73, 75, 76, 77; 81/460

[56] References Cited

U.S. PATENT DOCUMENTS

| | | |
|---|---|---|
| 2,814,296 | 11/1957 | Everett . |
| 3,494,243 | 2/1970 | Kleinhenn ............................ 606/76 |
| 3,977,081 | 8/1976 | Zambelli . |
| 4,012,551 | 3/1977 | Bogaty et al. ...................... 428/192 |
| 4,275,813 | 6/1981 | Noiles ................................ 206/339 |
| 4,362,162 | 12/1982 | Nakajima et al. ................. 128/334 |
| 4,655,222 | 4/1987 | Florez et al. ...................... 128/334 |
| 4,788,979 | 12/1988 | Jarrett et al. ..................... 128/335.5 |
| 4,835,819 | 6/1989 | Duffy et al. ....................... 427/195 |
| 4,927,421 | 5/1990 | Goble ................................ 606/73 |
| 4,950,270 | 8/1990 | Bowman .............................. 606/72 |
| 5,053,036 | 10/1991 | Perren ............................... 606/77 |
| 5,062,843 | 11/1991 | Mahony ............................. 606/77 |
| 5,108,399 | 4/1992 | Eitenmuller ...................... 606/76 |

FOREIGN PATENT DOCUMENTS

| | | | |
|---|---|---|---|
| 9008510 | 8/1990 | WIPO | ................................ 606/104 |

OTHER PUBLICATIONS

Leslie S. Matthews, M.D. & Stephen R. Soffer, M.D., Pitfalls in the Use of Interference Screws for Anterior Cruciate Ligament Reconstruction: Brief Report, Published Arthroscopy, 1989.

*Primary Examiner*—Michael A. Brown

[57] ABSTRACT

A fastener including an elongated body having one or more ridges passing across its exterior surface intersecting root portions between them. Each ridge has a crest portion with edges bounded by distal and proximal slope portions extending inwardly from the crest edges to the root portions. A coating is disposed on the crest portion and at least part of the distal slope portion but not on at least part of the root portion. The coating has a selected coefficient of friction different from that of the exterior surface of the elongated body. The fastener further includes an element for engaging a driver to enable insertion of the elongated body into a tissue of the patient. The coating modifies the amount of force which must be applied to the driver to insert the fastener.

15 Claims, 1 Drawing Sheet

SURGICAL FASTENER WITH SELECTIVELY COATED RIDGES

This application is a Continuation of application Ser. No. 837,458 filed Feb. 14, 1992, now abandoned.

FIELD OF THE INVENTION

This invention relates to a fastener having at least one ridge partially coated with a coating having a selected coefficient of friction, and more particularly to such a fastener for surgical use.

BACKGROUND OF THE INVENTION

There are a number of surgical procedures in which a fastener such as a screw or nail is inserted into a tissue of a patient. One surgical use involves insertion of an interference screw into a bone tunnel to secure a bone plug in place to attach an end of an anterior cruciate ligament (ACL) replacement. ACL reconstruction procedures are disclosed in U.S. Pat. Nos. 5,062,843, 4,950,270 and 4,927,421, for example.

A relatively large amount of torque must be applied to an interference screw during insertion. Similarly, insertion of nails, tacks and other fasteners can require a large insertion force.

Coatings having a low coefficient of friction have been applied to a number of surgical devices including suture needles and hypodermic needles (U.S. Pat. No. 2,814,296), and surgical staples (U.S. Pat. No. 4,655,222). Typically, most or all of the exterior surface of these devices are coated with a low coefficient of friction material such as Teflon, available from E. I. du Pont de Nemours & Co.

Other uses of a Teflon-type material include incorporation into surgical sutures (U.S. Pat. No. 4,362,162), on razor blades (U.S. Pat. No. 4,012,551), and on screws to provide self-sealing fasteners (U.S. Pat. No. 3,494,243). Other uses include application of absorbable or nonabsorbable plastics (including polytetrafluoroethylene) to staples as disclosed in U.S. Pat. No. 4,275,813. Use of Teflon and other resins for resisting corrosion has been disclosed for dental implants in U.S. Pat. No. 3,977,081 and for threaded fasteners in U.S. Pat. No. 4,835,819.

A surgical screw or other fastener which exhibits an overall coefficient of friction which is a very low may be inadvertently over-tightened or over-inserted. Problems of tendon laceration by over-inserted interference screws are described for example in L. S. Matthews et al., "Pitfalls In The Use of Interference Screws For Anterior Cruciate Ligament Reconstruction: Brief Report", J. Arthroscopic and Related Surgery 5(3):225–226 (1989). Additionally, screws which have sharp threads can nick suture and tissue during emplacement.

None of the above references discloses or suggests selectively placing a coating on a portion of a fastener to lessen required insertion force while maintaining sufficient friction to minimize over-insertion or over-penetration of the fastener.

SUMMARY OF THE INVENTION

Therefore, it is an object of the invention to provide an improved fastener which provides a desirable "feel" or resistance to insertion.

It is a further object of the invention to provide a surgical screw for which the risk of over-insertion is minimized.

Yet another object of the invention is to provide such a surgical screw having sharp threads which are partially coated to lessen the risk of injury to tissue contacted before the screw is fully emplaced.

A still further object of the invention is to conserve the quantity of coating applied to a surgical fastener.

This invention features a fastener including an elongated body having one or more ridges passing across its exterior surface intersecting root or floor portions between them. Each ridge has a crest portion with edges bounded by distal and proximal slope portions extending inwardly from the crest edges to the root portions. A biocompatible coating is disposed on the crest portion and at least part of the distal slope portion but not on at least part of the root portion. The coating has a selected coefficient of friction different from that of the exterior surface of the elongated body. The fastener further includes an element for engaging a driver to enable insertion of the elongated body into a tissue of the patient. The coating modifies the amount of force which must be applied to the driver to insert the fastener.

In one embodiment, the coating is substantially absent from the root portion, and preferably extends no more than halfway inwardly from the crest portion toward the inwardmost point of the root portion. The coating has a lower coefficient of friction than the exterior surface of the elongated body, and is a Teflon-type or bioabsorbable material.

In one of the preferred embodiments, the fastener is an interference screw having a helical thread traversing the root portion and the coating extends from the crest portion partially down both the proximal and distal slope portions of the thread. The coating is comprised of spray-deposited Teflon or biocompatible material which is also deposited on a narrow-diameter tip portion of the screw. The screw lacks a head member such that the outer diameter of the helical thread is greater than the diameter of the proximal end of the screw. The proximal end of the screw defines a polygonal socket into which a matching tip of the driver is insertable.

BRIEF DESCRIPTION OF THE DRAWINGS

Other objects, features and advantages will occur from the following description of preferred embodiments and the accompanying drawings, in which.

DESCRIPTION OF THE PREFERRED EMBODIMENTS

Figure 1:
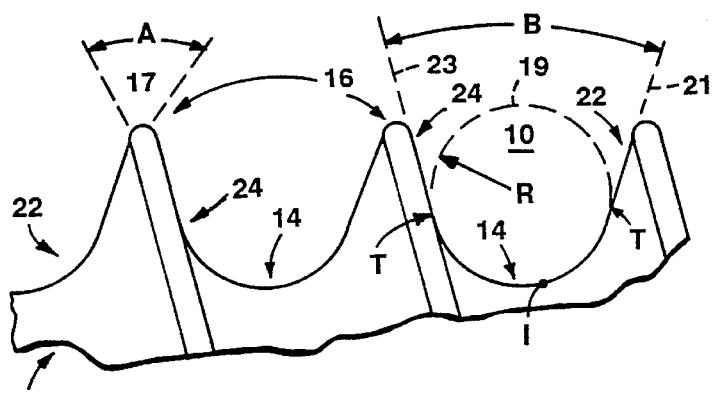
FIG. 1 is an enlarged, partial side view of a portion of an interference screw.

This invention may be accomplished by an interference screw 10, FIG. 1, having an elongated body 12 with a root portion 14 about its inner or minor diameter. The major or outer diameter of the screw 12 is formed by a helical thread 16 which traverses the root portion 14. The thread 16 is shown having a crest 17 bounded by edges 18, 20 which define between them arc "A". Proximal and distal slope portions 22, 24 lie between the crest 17 and root portion 14.

In this construction, the root portion 14 is arcuate having a curvature of radius R as indicated in phantom by circle 19. The curvature of the thread 16 changes at tangency point T, which is the intersection between line 21 of proximal slope 22 and line 23 of distal slope 24. Slope lines 21, 23 are relatively straight in this construction. Tangency points T occur approximately at the pitch diameter, that is, halfway between the major and minor diameters.

Figure 2:
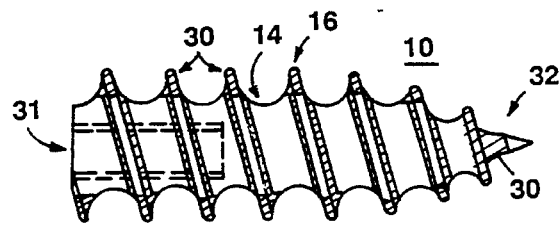
FIG. 2 is a side view of the interference screw of FIG. 1 selectively coated according to the present invention.

A biocompatible coating 30 is shown in FIG. 2 covering or enveloping the crest portion 17 and on the distal and proximal slope portions 22, 24. The root portion 14 lying between and intersected by the thread 16 remains uncoated. In this construction, screw 10 includes a distal tip 32 which is also covered with the coating 30.

A coating applied according to the present invention does not cover the entire root portion. Preferably, the coating extends inwardly along a thread or other ridge no more than halfway from the crest of the ridge to the inwardmost point I of the root portion as indicated in FIG. 1.

When the coating 30 is a Teflon-type material or other biocompatible material having a low coefficient of friction and the elongated body 12 is stainless steel or a titanium alloy having a higher coefficient of friction, the coating 30 reduces the amount of torque required to insert the screw 10. By leaving the root portion 14 exposed, the screw 10 provides a desirable amount of resistance during insertion to enable the surgeon to "feel" the amount of engagement between the screw and a bone into which it is being inserted. This "feel" is particularly important when the screw is being guided between the surface of a bone tunnel and a bone block to be wedged in a bone tunnel such as during ACL reconstruction.

Figure 3:
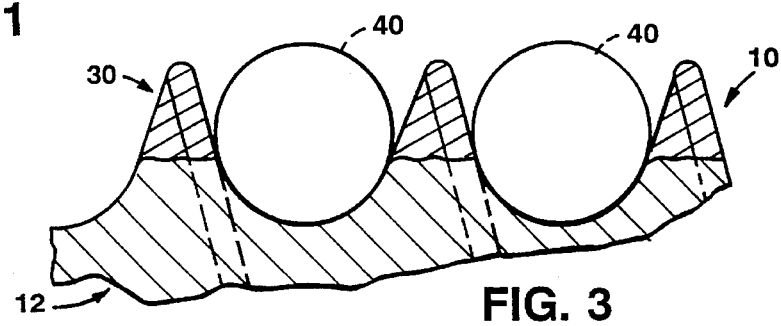
FIG. 3 is a partial cross-sectional view of the screw shown in FIG. 2 with masking wire.

One method of selectively applying the coating 30 is illustrated in FIG. 3. A brass wire 40 is wrapped about the screw body 12 to lie along the root portion 14. The screw 10 is placed upright by mounting the screw 10 on a post which engages the drive socket 31, FIG. 2. Teflon or other desired material then is conventionally spray coated onto the upright screw 10; the exterior of the screw 10 which is masked by the masking wire 40 remains uncoated. After conventional curing or drying, the screw 10 is removed from the vertical post and is unscrewed from the masking wire 40 using a driver.

Figure 4A:
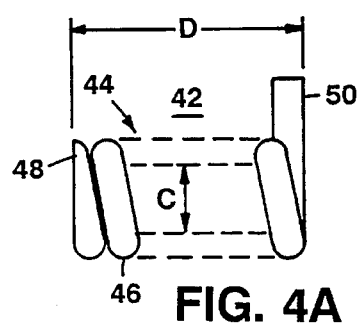
FIGS. 4A and 4B are schematic and side and end views respectively of a masking wire coil.
Figure 4B:
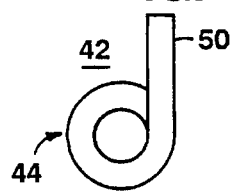

Instead of manually wrapping a straight wire about the elongated body of the fastener, a pre-formed masking spring coil 42, FIGS. 4A and 4B, can be used. The spring 42 includes a main body 44 formed of a wire 46 which terminates at one end in a tapered tip 48 and at the other end at an extension or tab 50.

To mask the root portion of a screw, the tip of the screw is rotatably inserted past the tapered tip 48 into the main body 44. The tab 50 is useful during insertion to position the spring mask 42 and prevent its rotation relative to the screw being inserted. During removal of the screw, the tab 50 serves as a lever to slightly untwist and expand the spring 42 to assist removal from the now coated screw.

Dimensions for one type of screw and masking coil are as follows. For an interference screw having a major diameter of 9 mm (0.354 inch), a minor diameter of 0.216 inch, a pitch (distance between crests) of 0.110 inch and a thread angle B of thirty degrees, and a depth (vertical distance between root and crest) of 0.069 inch, the masking spring 42 has a inner diameter C of 0.216 inch (which matches the minor diameter of the screw), a diameter of wire 46 of 0.080 inch, and a length D of approximately 0.7 to 1.1 inch depending on the length of the screw. Similarly, a screw having a major diameter of 7 mm (0.276 inch) and a minor diameter of 0.138 inch would utilize a masking spring having an inner diameter C of 0.138 inch. For a screw having a square thread, a masking coil formed of a square wire can be utilized.

Figure 5:
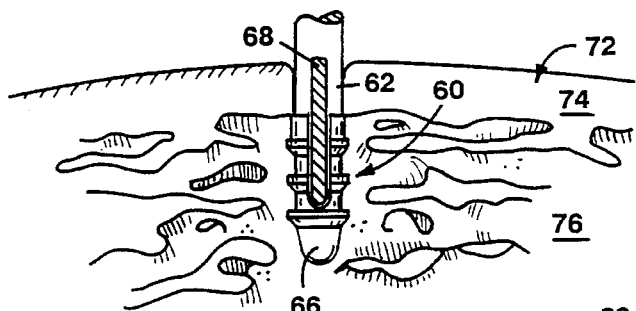
FIG. 5 is a schematic side view of another fastener coated according to the present invention during insertion into a hole drilled in a bone.

Another fastener which can be coated according to the present invention is shown in FIG. 5 during insertion into a bone 72. A suture anchor 60 is shown interlocked with a driver shaft 62 and carrying a suture 68. The bone 72 is formed of an outer cortical layer 74 and an inner cancellous layer 76.

Figure 6:
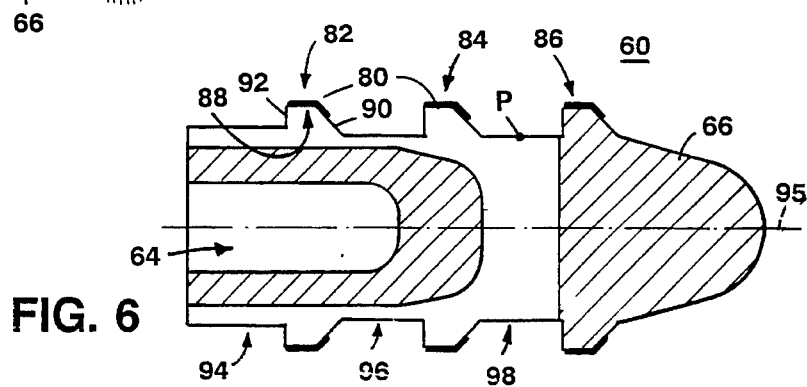
FIG. 6 is a side cross-sectional view of the fastener shown in FIG. 5.

The anchor 60 is shown in FIG. 6 in cross-section to illustrate a coating 80 disposed on a portion of ridges 82, 84 and 86. Each ridge includes a crest portion 88, a distal slope portion 90 and a proximal slope portion 92. Root portions 94, 96 and 98 lie between the ridges 82, 84 and 86 and are parallel to longitudinal axis 95.

The coating 80 covers the crest portions 88 and part of the distal slope portions 90 which are the regions that slide past and generate friction against the cortical region 74 of the bone 72. The proximal slope portions 92 and the root portion 94, 96, 98 and the distal tip 66 remain uncoated. The inwardmost, center point P of the root portion 98 is illustrated for reference.

The anchor 60 further includes a driver engagement socket 64 at its proximal end and a rounded tip 66 at its distal end. Instead of a drive socket 64, a flat head can be provided at the proximal end to be impacted by a mallet to accomplish the linear insertion of the suture anchor or similar fastener. The driver shaft 62 can include a stop member to limit the depth of insertion.

One technique by which the coating 80 could be applied utilizes bands of metal that are wrapped about the root portion 96 and 98. Suitably configured cylindrical caps are separately placed over tip 66 and proximal root portion 94.

The type of coating to be deposited according to the present invention on a fastener depends on the overall desired coefficient of friction of the fastener. If the fastener has an undesirably low coefficient of friction and inserts too easily, a coating having a higher coefficient can be selectively applied. Further, the coating can have a selected dissolution or erosion rate upon contact with bodily fluids.

Nonabsorbable Teflon is desired for lessening the overall coefficient of friction of a stainless steel or titanium alloy screw as described above. Alternative nonabsorbable coatings which may be acceptable for certain applications include Parylene-C available from Nova Tran Corporation of Clearlake, Wis. Parylene-C is marketed as a sealant and guards against moisture. Other possible alternatives include silicone, Hypan from Kinston Technologies, Dayton, N.J., and "Diamond-Like Carbon" coating available from Diamonex, Inc., Allentown, Pa.

Bioabsorbable coatings include polycaprolate and others such as disclosed in U.S. Pat. No. 4,788,979, incorporated herein by reference. One acceptable polycaprolate is a random copolymer of 85 weight percent epsilon-caprolactone and 15 weight percent glycolide.

A bioabsorbable coating can be applied over a bioabsorbable bone screw such as the screw disclosed in German Patent No. DE 3,811,345. Other absorbable surgical devices are disclosed in U.S. Pat. Nos. 4,300,565 (Rosensaft et al.) and 4,429,080 (Casey et al.), incorporated herein by reference. One consideration to be made for absorbable coatings is that, if the coating dissolves too rapidly, the coating will not be present to assist removal and repositioning of the screw if desired.

The configuration of a fastener may affect the desired type of coating: a helical thread provides greater surface area in contact with a bone or other tissue than circumferential ridges of the fastener shown in FIGS. 5 and 6. The amount and type of material in contact with the tissue will affect the "feel" of the device to the surgeon. Several examples are provided below to illustrate the effects of selective coating according to the present invention.

EXAMPLE 1

Three uncoated, titanium alloy (ASTM F-136) screws lacking a head member and having a major diameter of 7 mm, a length 25 mm, a minor diameter of 0.138 inch, a thread pitch of thirty degrees, and a thread depth of 0.069 inch were separately inserted into separate holes drilled in bovine bone. Each hole had a diameter of 0.125 inch. Each hole and screw were maintained moist with water during insertion. The results for the three baseline screws are presented in Table 1. The average torque was 10.9 In. Lbs.

TABLE 1

| SCREW | MAX. TORQUE | DEPTH | OBSERVED SOUND |
| --- | --- | --- | --- |
| BASELINE | | | |
| 1A | 12 In.Lbs. | 15 mm | Squeak |
| 1B | 9.8 In.Lbs. | 15 mm | Squeak |
| 1C | 11 In.Lbs. | 15 mm | Squeak |
| 100% TEFLON | | | |
| 2A | 2.4 In.Lbs. | 15 mm | None |
| 2B | 3.4 In.Lbs. | 15 mm | None |
| 2C | 2.8 In.Lbs. | 15 mm | None |
| MASKED TEFLON | | | |
| 3A | 8.2 In.Lbs. | 15 mm | Slight Squeak |
| 3B | 6.8 In.Lbs. | 15 mm | Slight Squeak |
| 3C | 6.4 In.Lbs. | 15 mm | Slight Squeak |
| 100% PARYLENE-C | | | |
| 4A | 3.4 In.Lbs. | 15 mm | None |
| 4B | 2.6 In.Lbs. | 15 mm | None |
| 4C | 3.4 In.Lbs. | 15 mm | None |

EXAMPLE 2

Three screws having a major diameter of 7 mm and a length of 20 mm were one-hundred percent coated with Teflon 959-205 from Du Pont. The Teflon was conventionally applied by spraying, and conventionally dried. The resulting coating had a thickness of approximately 0.0008–0.0010 inch. Tests were conducted as presented in Example 1 and the results are as presented in Table 1. The average torque was 2.8 In. Lbs.

EXAMPLE 3

Three 7 mm by 20 mm screws identical to those of Example 2 were masked with a brass wire so that only 0.10 inch of the distal tip and part of the threads were covered with Teflon as shown in FIG. 3. The coating had a thickness of approximately 0.0008–0.0010 inch. Tests were conducted as set forth in Example 1 and the results are presented in Table 1. The average torque was 7.1 In. Lbs.

EXAMPLE 4

Three screws were conventionally coated completely with Parylene-C, the screws having a major diameter of 7 mm and a length of 25 mm. The coating had a thickness of approximately 0.0008–0.0010 inch. Tests were conducted as described in Example 1 and the results are presented in Table 1. The average insertion torque was 3.1 In. Lbs.

In summary, the uncoated screws of Example 1 provided the most positive feel, that is, resistance, during insertion. The one-hundred percent coated Teflon and Parylene-C provided very little resistance during insertion and therefore potentially could be over-inserted. The masked screws provided a slight resistance and a slight "squeak" sound which provided desirable feedback during its insertion to the operator of the driver.

Although specific features of the invention are shown in some drawings and not in others, this is for convenience only as each feature may be combined with any or all of the other features in accordance with the invention.

Other embodiments will occur to those skilled in the art and are within the following claims.

What is claimed is:

1. A fastener for surgical use, comprising:
   an elongated body having a distal end and a proximal end and defining a root portion on its exterior surface extending between said distal and proximal ends, said body further defining at least one ridge intersecting said root portion and extending outwardly from said body, said ridge having a crest portion with edges bounded by distal and proximal slope portions extending inwardly from said crest edges to said root portion;
   means, disposed at said proximal end, for engaging a driver to enable insertion of said body into a tissue of a patient; and
   a biocompatible coating disposed on said crest portion and at least part of said distal slope portion but not on at least part of said root portion, said coating having a selected coefficient of friction different from that of said exterior surface of said body to modify driver force to be applied for insertion of said fastener.

2. The fastener of claim 1 in which said coating is absent from said root portion.

3. The fastener of claim 1 in which said coating extends no more than halfway inwardly from said crest portion toward the inwardmost point of said root portion.

4. The fastener of claim 1 in which said coating has a lower coefficient of friction than said exterior surface of said body.

5. The fastener of claim 4 in which said coating is a Teflon type material.

6. The fastener of claim 4 in which said coating is a bioabsorbable material.

7. A screw for surgical use, comprising:
   an elongated screw body having a distal end and a proximal end and defining a root portion on its exterior surface extending between said distal and proximal ends, said screw body further defining a helical thread traversing said root portion and extending outwardly from said screw body, said thread having a crest portion with edges bounded by slope portions extending inwardly from said crest edges distal and proximal to said root portion;
   means, disposed at said proximal end, for engaging a driver to enable rotatable insertion of said screw body into a tissue of a patient; and a biocompatible coating disposed on said crest portion and at least part of said distal and proximal slope portions but not on at least part of said root portion, said coating having a selected coefficient of friction different from that of said exterior surface of said screw body to modify driver torque to be applied for insertion of said screw.

8. The screw of claim 7 in which said coating is substantially absent from said root portion.

9. The screw of claim 7 in which said coating extends no more than halfway inwardly from said crest toward the inwardmost point of said root portion.

10. The screw of claim 7 in which said coating has a lower coefficient of friction than said exterior surface of said body.

11. The screw of claim 10 in which said coating is a Teflon type material.

12. The screw of claim 10 in which said coating is a bioabsorbable material.

13. The screw of claim 7 in which said coating is comprised of spray-deposited material.

14. The screw of claim 7 in which said screw body includes a narrow-diameter tip portion at said distal end, and said coating is further disposed on at least part of said tip portion.

15. The screw of claim 7 in which said screw lacks a head member such that the outer diameter of said helical thread is greater than the diameter of said proximal end.

* * * * *